United States Patent
Desario

[11] Patent Number: 5,749,377
[45] Date of Patent: May 12, 1998

[54] PEDICURE KIT

[76] Inventor: Alphonse J. Desario, 205 Montreal Ave., Staten Island, N.Y. 10306

[21] Appl. No.: 705,174

[22] Filed: Aug. 29, 1996

[51] Int. Cl.$^6$ ............................ A45D 29/18; A45D 29/22
[52] U.S. Cl. ................... 132/73.5; 132/286; 132/73; 30/29
[58] Field of Search ..................... 132/73, 73.5, 75.3, 132/75.4, 75.5, 286; 30/26, 27, 28, 29, 123; 128/882, 829; D28/56, 57, 60, 61, 62

[56] References Cited

U.S. PATENT DOCUMENTS

| D. 286,091 | 10/1986 | Hill | D28/60 |
|---|---|---|---|
| 857,790 | 6/1907 | Carroll | 30/29 |
| 2,517,232 | 8/1950 | Patulski | 132/73 |
| 2,676,597 | 4/1954 | Colbert | 132/73 |
| 4,847,994 | 7/1989 | Dunn, Jr. | 30/28 |
| 4,893,406 | 1/1990 | Larson | 30/28 |
| 5,326,056 | 7/1994 | Smith | 132/73 |
| 5,357,677 | 10/1994 | West | 30/28 |

FOREIGN PATENT DOCUMENTS

| 1027346 | 5/1953 | France | 132/73 |
|---|---|---|---|
| 959853 | 3/1957 | Germany | 30/28 |
| 525059 | 8/1940 | United Kingdom | 132/73 |
| 2240297 | 7/1991 | United Kingdom | 132/73.5 |

Primary Examiner—Todd E. Manahan
Attorney, Agent, or Firm—Richard L. Miller, P.E.

[57] ABSTRACT

A pedicure kit comprises a toe spreader and a toe nail scissor that separates toes of a foot of a user who has difficulty bending without the user having to bend and cuts the toe nails on the toes of the foot of the user who has difficulty bending without the user having to bend. The combination includes an elongated and slender toe spreader, and an elongated and slender toe nail scissor. The elongated and slender toe spreader has a slender handle portion that is releasibly engagable in the palm of a hand of the user, and a toe spreader portion that is remote from the slender handle portion of the elongated and slender toe spreader and releasibly engages and separates the toes of the foot of the user from each other without the user having to bend, so that the toes of the foot of the user who has difficulty bending can be separated from each other without the user having to bend and separate the toes of the foot of the user with another hand of the user. And, the elongated and slender toe nail scissor is separate from the elongated and slender toe spreader and has a handle portion that is releasibly engagable by the thumb and the index finger of another hand of the user, and a cutting portion that is remote from the handle portion of the elongated and slender toe nail scissor and cuts the toe nails on the toes of the foot of the user without the user having to bend, so that the toe nails on the toes of the foot of the user who has difficulty bending can be cut without the user having to bend.

25 Claims, 1 Drawing Sheet

PEDICURE KIT

BACKGROUND OF THE INVENTION

The present invention relates to a combination toe spreader and toe nail scissor. More particularly, the present invention relates to a combination toe spreader and toe nail scissor that separates toes of a foot of a user who has difficulty bending without the user having to bend and cuts the toe nails on the toes of the foot of the user who has difficulty bending without the user having to bend. The combination includes an elongated and slender toe spreader, and an elongated and slender toe nail scissor. The elongated and slender toe spreader has a slender handle portion that is releasibly engagable in the palm of a hand of the user, and a toe spreader portion that is remote from the slender handle portion of the elongated and slender toe spreader and releasibly engages and separates the toes of the foot of the user from each other without the user having to bend, so that the toes of the foot of the user who has difficulty bending can be separated from each other without the user having to bend and separate the toes of the foot of the user with another hand of the user. And, the elongated and slender toe nail scissor is separate from the elongated and slender toe spreader and has a handle portion that is releasibly engagable by the thumb and the index finger of another hand of the user, and a cutting portion that is remote from the handle portion of the elongated and slender toe nail scissor and cuts the toe nails on the toes of the foot of the user without the user having to bend, so that the toe nails on the toes of the foot of the user who has difficulty bending can be cut without the user having to bend.

Many older individuals, overweight individuals, and physically disabled individuals have extreme difficulty in trimming their toe nails with conventional forms of toe nail clippers. In fact, many individuals find it entirely impossible to trim their toe nails with these conventional devices and are forced to seek assistance in trimming their toe nails.

Numerous innovations for toe nail clipping assisting devices have been provided in the prior art that will be described. Even though these innovations may be suitable for the specific individual purposes to which they address, however, they differ from the present invention in that they do not teach a combination toe spreader and toe nail scissor that separates toes of a foot of a user who has difficulty bending without the user having to bend and cuts the toe nails on the toes of the foot of the user who has difficulty bending without the user having to bend. The combination includes an elongated and slender toe spreader, and an elongated and slender toe nail scissor. The elongated and slender toe spreader has a slender handle portion that is releasibly engagable in the palm of a hand of the user, and a toe spreader portion that is remote from the slender handle portion of the elongated and slender toe spreader and releasibly engages and separates the toes of the foot of the user from each other without the user having to bend, so that the toes of the foot of the user who has difficulty bending can be separated from each other without the user having to bend and separate the toes of the foot of the user with another hand of the user. And, the elongated and slender toe nail scissor is separate from the elongated and slender toe spreader and has a handle portion that is releasibly engagable by the thumb and the index finger of another hand of the user, and a cutting portion that is remote from the handle portion of the elongated and slender toe nail scissor and cuts the toe nails on the toes of the foot of the user without the user having to bend, so that the toe nails on the toes of the foot of the user who has difficulty bending can be cut without the user having to bend.

For example, U.S. Pat. No. 4,847,994 to Dunn, Jr. teaches a remotely actuated toe nail clipper that includes a cylindrical tubular housing which encloses an axially reciprocating plunger rod. A leaf spring type toe nail clipper extends through a slot in a bottom portion of the housing. An actuating lever of the toe nail clipper is in engagement with the plunger rod. A scissor mechanism extends transversely through a slot in an upper portion of the housing for actuating the plunger rod. The device is particularly designed for use by individuals who have difficulty reaching their toe nails with conventional forms of nail clippers. In a second embodiment, the axially movable plunger rod is electrically actuated by a solenoid mechanism. An adjustable telescope is mounted in parallel relation to the cylindrical housing and provides an individual with a clear view of the toe nail clipper.

Another example, U.S. Pat. No. 4,893,406 to Larson teaches an extension apparatus in combination with a conventional nail clipping device. The extension apparatus comprises an elongated extension member and a remote actuating unit which are operatively connected to the conventional nail clipping device. The extension member is further provided with a visual inspection member and a support member.

Finally, still another example, U.S. Pat. No. 5,357,677 to West teaches a toe nail clipper apparatus that has a nail clipper connected on one end of an elongated member and a pistol-type grip mounted on the other end. A cord attached to the nail clipper and a trigger adjacent to the handle actuates the clipper. The elongated member may have a pivotal joint near the clipper end of the elongated member to permit moving the clipper in an arc.

It is apparent that numerous innovations for toe nail clipping assisting devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

Accordingly, an object of the present invention is to provide a combination toe spreader and toe nail scissor that avoids the disadvantages of the prior art.

Another object of the present invention is to provide a combination toe spreader and toe nail scissor that is simple and inexpensive to manufacture.

Still another object of the present invention is to provide a combination toe spreader and toe nail scissor that is simple to use.

Yet another object of the present invention is to provide a combination toe spreader and toe nail scissor that would by found very useful by people with back problems for cutting their nails.

Still yet another object of the present invention is to provide a combination toe spreader and toe nail scissor that keeps toes apart when the toe nails are being cut.

Briefly stated, yet still another object of the present invention is to provide a combination toe spreader and toe nail scissor that separates toes of a foot of a user who has difficulty bending without the user having to bend and cuts the toe nails on the toes of the foot of the user who has difficulty bending without the user having to bend, the user has a hand with a palm, another hand with a thumb and an index finger, and the foot of the user has a side and a ball, wherein the combination includes an elongated and slender toe spreader, and an elongated and slender toe nail scissor.

Still yet another object of the present invention is to provide a combination toe spreader and toe nail scissor wherein the elongated and slender toe spreader has a slender handle portion that is releasibly engagable in the palm of the hand of the user, and a toe spreader portion that is remote from the slender handle portion of the elongated and slender toe spreader and releasibly engages and separates the toes of the foot of the user from each other without the user having to bend, so that the toes of the foot of the user who has difficulty bending can be separated from each other without the user having to bend and separate the toes of the foot of the user with the another hand of the user.

Yet still another object of the present invention is to provide a combination toe spreader and toe nail scissor wherein the elongated and slender toe nail scissor is separate from the elongated and slender toe spreader and has a handle portion that is releasibly engagable by the thumb and the index finger of the another hand of the user, and a cutting portion that is remote from the handle portion of the elongated and slender toe nail scissor and cuts the toe nails on the toes of the foot of the user without the user having to bend, so that the toe nails on the toes of the foot of the user who has difficulty bending can be cut without the user having to bend.

Still yet another object of the present invention is to provide a combination toe spreader and toe nail scissor wherein the elongated and slender toe spreader has a length that extends from the palm of the hand of the user to the toes of the foot of the user, so that the toes of the foot of the user can be separated from each other without the user having to bend.

Yet still another object of the present invention is to provide a combination toe spreader and toe nail scissor wherein the length of the elongated and slender toe spreader is 42".

Still yet another object of the present invention is to provide a combination toe spreader and toe nail scissor wherein the elongated and slender toe spreader further has an elongated, slender, and generally rectangular-parallelepiped-shaped body with a proximal end from which the slender handle portion of the elongated and slender toe spreader extends coplanarally upwardly, and a distal end from which the toe spreader portion of the elongated and slender toe spreader extends coplanarally downwardly.

Yet still another object of the present invention is to provide a combination toe spreader and toe nail scissor wherein the slender handle portion of the elongated and slender toe spreader is narrower than the elongated, slender, and generally rectangular-parallelepiped-shaped body of the elongated and slender toe spreader so as to provide a pair of lateral shoulders, so that a stop is provided when the palm of the hand of the user grips the slender handle portion of the elongated and slender toe spreader that prevents downward slipping thereof.

Still yet another object of the present invention is to provide a combination toe spreader and toe nail scissor wherein the toe spreader portion of the elongated and slender toe spreader is slightly deformable, so that the toes of the foot of the user of different sizes can be adjusted for.

Yet still another object of the present invention is to provide a combination toe spreader and toe nail scissor wherein the slightly deformable toe spreader portion of the elongated and slender toe spreader is rubber.

Still yet another object of the present invention is to provide a combination toe spreader and toe nail scissor wherein the toe spreader portion of the elongated and slender toe spreader has a generally isosceles-triangular-shaped upper part with an isosceles triangular shape.

Yet still another object of the present invention is to provide a combination toe spreader and toe nail scissor wherein the isosceles triangular shape of the generally isosceles-triangular-shaped upper part of the toe spreader portion of the elongated and slender toe spreader provides an even distribution of a downward force exerted on the toes of the foot of the user by the hand of the user pushing downwardly on the slender handle portion of the elongated and slender toe spreader, so that the toes of the foot of the user can be easily separated from each other.

Still yet another object of the present invention is to provide a combination toe spreader and toe nail scissor wherein the generally isosceles-triangular-shaped upper part of the toe spreader portion of the elongated and slender toe spreader has a flat apex that is equivalently configured to the distal end of the elongated, slender, and generally rectangular-parallelepiped-shaped body of the elongated and slender toe spreader with the generally isosceles-triangular-shaped upper part of the toe spreader portion of the elongated and slender toe spreader extending coplanarally downwardly therefrom, a pair of straight and upwardly tapering sides that have lower ends and extend downwardly and outwardly from each end of the flat apex of the generally isosceles-triangular-shaped upper part of the toe spreader portion of the elongated and slender toe spreader, and a straight base that has a length to extend past three separated middle toes of the toes of the foot of the user, so that the elongated and slender toe spreader can be utilized on the foot of the user of different widths.

Yet still another object of the present invention is to provide a combination toe spreader and toe nail scissor wherein the straight base of the generally isosceles-triangular-shaped upper part of the toe spreader portion of the elongated and slender toe spreader connects the lower ends of the pair of straight and upwardly tapering sides of the generally isosceles-triangular-shaped upper part of the toe spreader portion of the elongated and slender toe spreader to each other.

Still yet another object of the present invention is to provide a combination toe spreader and toe nail scissor wherein the straight base of the generally isosceles-triangular-shaped upper part of -the toe spreader portion of the elongated and slender toe spreader is 5" long.

Yet still another object of the present invention is to provide a combination toe spreader and toe nail scissor wherein the toe spreader portion of the elongated and slender toe spreader further has a generally rectangular-parallelepiped-shaped lower part that extends downwardly from, and is integrally formed with, the straight base of the generally isosceles-triangular-shaped upper part of the toe spreader portion of the elongated and slender toe spreader, is coplanar with the generally isosceles-triangular-shaped upper part of the toe spreader portion of the elongated and slender toe spreader, and has a length equivalent to that of the straight base of the generally isosceles-triangular-shaped upper part of the toe spreader portion of the elongated and slender toe spreader.

Still yet another object of the present invention is to provide a combination toe spreader and toe nail scissor wherein the rectangular-parallelepiped-shaped lower part of the toe spreader portion of the elongated and slender toe spreader further has a straight lower edge, and a pair of spaced-apart, parallel, and generally rectangular-shaped faces that extend from the straight base of the generally isosceles-triangular-shaped upper part of the toe spreader portion of the elongated and slender toe spreader to the straight lower edge of the generally rectangular-parallelepiped-shaped lower part of the toe spreader portion of the elongated and slender toe spreader, and are coplanar with the generally isosceles-triangular-shaped upper part of the toe spreader portion of the elongated and slender toe spreader.

Yet still another object of the present invention is to provide a combination toe spreader and toe nail scissor wherein the straight lower edge of the rectangular-parallelepiped-shaped lower part of the toe spreader portion of the elongated and slender toe spreader has three spaced-apart and generally rectangular-shaped lateral toe throughslots.

Still yet another object of the present invention is to provide a combination toe spreader and toe nail scissor wherein each toe slot of the three spaced-apart and generally rectangular-shaped lateral toe throughslots in the straight lower edge of the generally rectangular-parallelepiped-shaped lower part of the toe spreader portion of the elongated and slender toe spreader has a width slightly less than that of a toe of the toes of the foot of the user, so that the elongated and slender toe spreader can be used with the toes of the foot of the user of different sizes.

Yet still another object of the present invention is to provide a combination toe spreader and toe nail scissor wherein the width of each toe slot of the three spaced-apart and generally rectangular-shaped lateral toe throughslots in the straight lower edge of the generally rectangular-parallelepiped-shaped lower part of the toe spreader portion of the elongated and slender toe spreader is 1".

Still yet another object of the present invention is to provide a combination toe spreader and toe nail scissor wherein the three spaced-apart and generally rectangular-shaped lateral toe throughslots in the straight lower edge of the generally rectangular-parallelepiped-shaped lower part of the toe spreader portion of the elongated and slender toe spreader open into, and extend vertically upwardly from, the straight lower edge of the generally rectangular-parallelepiped-shaped lower part of the toe spreader portion of the elongated and slender toe spreader to the straight base of the generally isosceles-triangular-shaped upper part of the toe spreader portion of the elongated and slender toe spreader, and extend laterally between, and open into, the pair of spaced-apart, parallel, and generally rectangular-shaped faces of the generally rectangular-parallelepiped-shaped lower part of the toe spreader portion of the elongated and slender toe spreader.

Yet still another object of the present invention is to provide a combination toe spreader and toe nail scissor wherein the elongated and slender toe nail scissor has a length that extends from the thumb and the index finger of the another hand of the user to the toes of the foot of the user, so that the toe nails on the toes of the foot of the user can be cut without the user having to bend.

Still yet another object of the present invention is to provide a combination toe spreader and toe nail scissor wherein the length of the elongated and slender toe nail scissor is 42".

Yet still another object of the present invention is to provide a combination toe spreader and toe nail scissor wherein the elongated and slender toe nail scissor has a pair of elongated and slender bodies that each have a length equivalent to combined length of the slender handle portion of the elongated and slender toe spreader and the elongated, slender, and generally rectangular-parallelepiped-shaped body of the elongated and slender toe spreader.

Still yet another object of the present invention is to provide a combination toe spreader and toe nail scissor wherein each body of the pair of elongated and slender bodies of the elongated and slender toe nail scissor has a proximal end from which each handle portion of the elongated and slender toe nail scissor outwardly extends.

Yet still another object of the present invention is to provide a combination toe spreader and toe nail scissor wherein each handle portion of the elongated and slender toe nail scissor is a closed finger loop that extends outwardly from, and is coplanar with, the proximal end of a respective body of the pair of elongated and slender bodies of the elongated and slender toe nail scissor, and has a diameter sufficient to releasibly capture one of the thumb and the index finger of the another hand of the user, so that the elongated and slender toe nail scissor is maintained in the another hand of the user during use and is prevented from dropping therefrom.

Still yet another object of the present invention is to provide a combination toe spreader and toe nail scissor wherein each body of the pair of elongated and slender bodies of the elongated and slender toe nail scissor further has a distal end.

Yet still another object of the present invention is to provide a combination toe spreader and toe nail scissor wherein the distal end of each body of the pair of elongated and slender bodies of the elongated and slender toe nail scissor are pivotally connected to each other by a pivot pin that maintains the closed finger loop of each handle portion of the elongated and slender toe nail scissor in opposing alignment with, and in movable relationship to, each other.

Still yet another object of the present invention is to provide a combination toe spreader and toe nail scissor wherein the cutting portion of the elongated and slender toe nail scissor has a height equivalent to that of the toe spreader portion of the elongated and slender toe spreader, and includes a pair of substantially L-shaped bodies.

Yet still another object of the present invention is to provide a combination toe spreader and toe nail scissor wherein each body of the pair of substantially L-shaped bodies of the cutting portion of the elongated and slender toe nail scissor has a vertical part with a lower end and which is integrally formed with, and extends vertically downwardly from, the distal end of a respective body of the pair of elongated and slender bodies of the elongated and slender toe nail scissor, with the vertical part of a respective body of the pair of substantially L-shaped bodies of the cutting portion of the elongated and slender toe nail scissor being coplanar with the respective body of the pair of elongated and slender bodies of the elongated and slender toe nail scissor.

Still yet another object of the present invention is to provide a combination toe spreader and toe nail scissor wherein each body of the pair of substantially L-shaped bodies of the cutting portion of the elongated and slender toe nail scissor further has an outwardly converging pointed horizontal cutting part that is integrally formed with, and extends generally perpendicularly horizontally outwardly from, the lower end of the vertical part of the respective body of the pair of substantially L-shaped bodies of the cutting portion of the elongated and slender toe nail scissor, with the outwardly converging pointed horizontal cutting part of the respective body of the pair of substantially L-shaped bodies of the cutting portion of the elongated and slender toe nail scissor being coplanar with the vertical part of the respective body of the pair of substantially L-shaped bodies of the cutting portion of the elongated and slender toe nail scissor, being coplanar with the closed finger loop of each the handle portion of the elongated and slender toe nail scissor, and pointing in the same direction as each other, so that the toe nails on the toes of the foot of the user can be cut from the side of the foot of the user without the user having to bend.

Yet still another object of the present invention is to provide a combination toe spreader and toe nail scissor that further includes a foot pad that is trapezoidal-shaped, has a length that extends transversely across the ball of the foot of the user, and a width that extends longitudinally along the ball of the foot of the user, so that a comfortable place is provided to rest the foot of the user when the toe nails on the toes of the foot of the user are being cut, while elevating the toes of the foot of the user.

Still yet another object of the present invention is to provide a combination toe spreader and toe nail scissor wherein the foot pad is rubber.

Finally, yet still another object of the present invention is to provide a method of using a combination toe spreader and toe nail scissor that separates toes of a foot of a user who has difficulty bending without the user having to bend and cuts the toe nails on the toes of the foot of the user who has difficulty bending without the user having to bend, the foot of the user has a ball and the toes of the foot of the user have tops and the user further has a hand with a palm and another hand with a thumb and an index finger, the method includes the steps of placing a user foot pad of the combination toe spreader and toe nail scissor on a generally horizontal surface; placing the foot of the user on the foot pad, with the ball of the foot of the user resting thereon; holding a handle portion of an elongated and slender toe spreader of the combination toe spreader and toe nail scissor in the palm of the hand of the user, with the elongated and slender toe spreader pointing downwardly; holding a handle portion of an elongated and slender toe nail scissor of the combination toe spreader and toe nail scissor in the another hand of the user, with a closed finger loop of each the handle portion of the elongated and slender toe nail scissor receiving one of the thumb and the index finger of the another hand of the user, and with the elongated and slender toe nail scissor pointing downwardly; positioning a straight lower edge of a generally rectangular-parallelepiped-shaped lower part of a toe spreader portion of the elongated and slender toe spreader on the tops of the toes of the foot of the user; exerting a downward force on the elongated and slender toe spreader and thereby cause three spaced-apart and generally rectangular-shaped lateral toe throughslots in the straight lower edge of the generally rectangular-parallelepiped-shaped lower part of the toe spreader portion of the elongated and slender toe spreader to slightly deform accordingly, and capture, three middle toes of the toes of the foot of the user and thereby cause the three middle toes of the toes of the foot of the user to separate from each other, while vertical sides of the generally rectangular-parallelepiped-shaped lower part of the toe spreader portion of the elongated and slender toe spreader cause a first toe and a fifth toe of the toes of the foot of the user to separate from the separated three middle toes of the toes of the foot of the user, so that the toes of the foot of the user who has difficulty bending can be separated from each other without the user having to bend and hold the toes of the foot of the user apart with the another hand of the user; and, cutting the toe nails on the separated toes of the foot of the user with a cutting portion of the elongated and slender toe nail scissor without the user having to bend, so that the toe nails on the toes of the foot of the user who has difficulty bending can be cut without the user having to bend.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows.

List of Reference Numerals Utilized in the Drawing 10 combination toe spreader and toe nail scissor of the present invention
12 elongated and slender toe spreader
14 toe spreader slender handle portion
16 user hand palm
18 user hand
20 user
22 toe spreader portion
24 user foot toes
26 user foot
28 user foot ball
30 user foot pad
32 elongated and slender toe nail scissor
34 toe nail scissor handle portion
36 user hand thumb
38 user hand index finger
40 another user hand
41 toe nail scissor cutting portion
42 user foot toe nails
44 toe spreader elongated, slender, and generally rectangular-parallelepiped-shaped body
46 toe spreader body proximal end
50 toe spreader body distal end
51 toe spreader handle portion pair of lateral shoulders
52 toe spreader portion generally isosceles-triangular-shaped upper part
54 toe spreader portion upper part flat apex
56 toe spreader portion upper part pair of straight and upwardly tapering sides
58 toe spreader portion upper part straight base
60 toe spreader portion rectangular-parallelepiped-shaped lower part
62 toe spreader portion lower part straight lower edge
64 toe spreader portion lower part pair of spaced-apart, parallel, and rectangular-shaped faces
66 toe spreader portion lower part lower edge three spaced-apart and rectangular-shaped lateral toe throughslots 68 toe nail scissor pair of elongated and slender bodies
70 toe nail scissor body proximal end
72 toe nail scissor handle portion closed finger loop
74 toe nail scissor body distal end
76 toe nail scissor body distal end pivot pin
78 toe nail scissor cutting portion pair of substantially L-shaped bodies
80 toe nail scissor cutting portion body vertical part
82 toe nail scissor cutting portion body pointed horizontal cutting part

DETAILED DESCRIPTION OF THE PREFERRED EMBODIMENT

Figure 1:
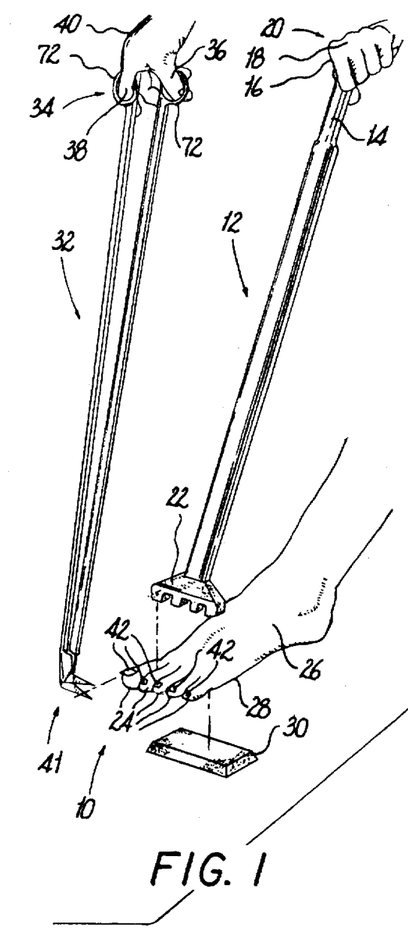
FIG. 1 is an exploded diagrammatic perspective view of the present invention interfacing with the toes of a user.
Figure 2:
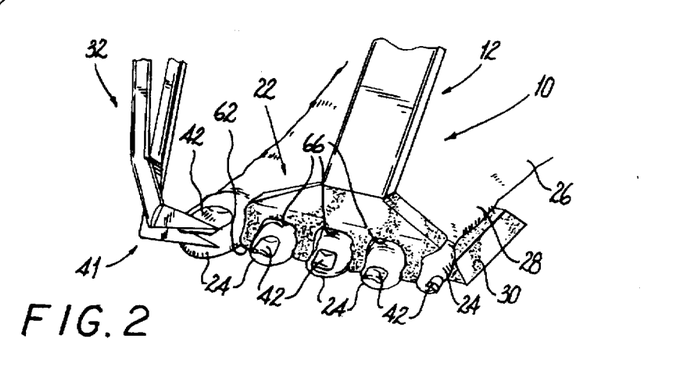
FIG. 2 is an enlarged diagrammatic perspective view of the present invention interfacing with the toes of a user.

Referring now to the figures in which like numerals indicate like parts, and particularly FIGS. 1 and 2, which are an exploded diagrammatic perspective view of the present invention interfacing with the toes of a user and an enlarged diagrammatic perspective view of the present invention interfacing with the toes of a user, respectively, the combination toe spreader and toe nail scissor of the present invention is shown generally at 10 and includes an elongated and slender toe spreader 12 that has a toe spreader slender handle portion 14 that is releasibly engagable in a user hand palm 16 of a user hand 18 of a user 20 and a toe spreader portion 22 that releasibly engages and separates user foot toes 24 of a user foot 26 of the user 20 from each other, while a user foot ball 28 of the user foot 26 of the user 20 rests on a user foot pad 30, and an elongated and slender toe nail scissor 32 that has a toe nail scissor handle portion 34 that is releasibly engagable by a user hand thumb 36 and a user hand index finger 38 of another user hand 40 of the user 20 and a toe nail scissor cutting portion 41 that cuts user foot toe nails 42 of the user foot toes 24 of the user foot 26 of the user 20.

The configuration of the user foot pad 30 can best be seen in FIGS. 1 and 2, which are an exploded diagrammatic perspective view of the present invention interfacing with the toes of a user and an enlarged diagrammatic perspective view of the present invention interfacing with the toes of a user, respectively, and as such will be discussed with reference thereto.

The user foot pad 30 is preferably rubber, trapezoidal-shaped, has a length that extends transversely across the user foot ball 28 of the user foot 26 of the user 20, and a width that extends longitudinally across the user foot ball 28 of the user foot 26 of the user 20, so that a comfortable place is provided to rest the user foot 26 of the user 20 when the user foot toe nails 42 of the user foot toes 24 of the user foot 26 of the user 20 are being cut, while elevating the foot toe 24 of the user foot 26 of the user 20.

Figure 3:
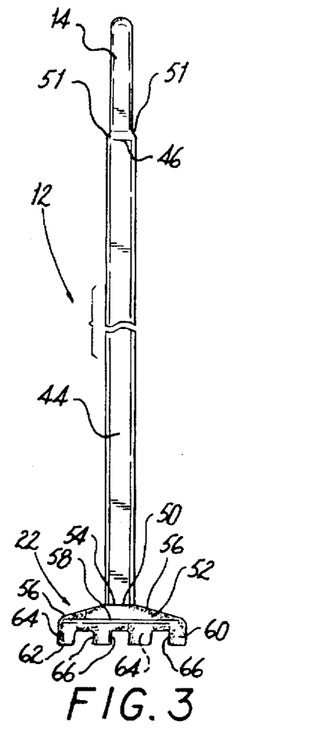
FIG. 3 is a diagrammatic side elevational view of the toe spreader of the present invention.

The configuration of the elongated and slender toe spreader 12 can best be seen in FIG. 3, which is a diagrammatic side elevational view of the toe spreader of the present invention, and as such will be discussed with reference thereto.

The elongated and slender toe spreader 12 has a length that extends from the user hand palm 16 of the user hand 18 of the user 20 to the user foot toes 24 of the user foot 26 of the user 20 and is thereby preferably 42" in length, so that the user foot toes 24 of the user foot 26 of the user 20 can be separated from each other without the user 20 having to bend.

The elongated and slender toe spreader 12 further has a toe spreader elongated, slender, and generally rectangular-parallelepiped-shaped body 44 with a toe spreader body proximal end 46 from which the toe spreader slender handle portion 14 of the elongated and slender toe spreader 12 extends coplanarally upwardly, and a toe spreader body distal end 50 from which the toe spreader portion 22 of the elongated and slender toe spreader 12 extends coplanarally downwardly.

The toe spreader elongated, slender, and generally rectangular-parallelepiped-shaped body of the elongated and slender toe spreader 12 and the integrally formed toe spreader slender handle portion 14 of the elongated and slender toe spreader 12 are made from a rigid material.

The toe spreader slender handle portion 14 of the elongated and slender toe spreader 12 is narrower than the toe spreader elongated, slender, and generally rectangular-parallelepiped-shaped body 44 of the elongated and slender toe spreader 12 and thereby provides a toe spreader handle portion pair of lateral shoulders 51, so that a stop is provided when the user hand palm 16 of the user hand 18 of the user 20 grips the toe spreader slender handle portion 14 of the elongated and slender toe spreader 12 that prevents downward slipping thereof.

The toe spreader portion 22 of the elongated and slender toe spreader 12 is slightly deformable, and is preferably rubber, so that the user foot toes 24 of the user foot 26 of the user 20 of different sizes can be adjusted for.

The toe spreader portion 22 of the elongated and slender toe spreader 12 has a toe spreader portion generally isosceles-triangular-shaped upper part 52. The isosceles triangular shape of the toe spreader portion generally isosceles-triangular-shaped upper part 52 of the toe spreader portion 22 of the elongated and slender toe spreader 12 provides an even distribution of the downward force exerted on the user foot toes 24 of the user foot 26 of the user 20 by the user hand 18 of the user 20 pushing downwardly on the toe spreader slender handle portion 14 of the elongated and slender toe spreader 12, so that the user foot toes 24 of the user foot 26 of the user 20 can be easily separated from each other.

The toe spreader portion generally isosceles-triangular-shaped upper part 52 of the toe spreader portion 22 of the elongated and slender toe spreader 12 has a toe spreader portion upper part flat apex 54 that is equivalently configured to the toe spreader body distal end 50 of the toe spreader elongated, slender, and generally rectangular-parallelepiped-shaped body of the toe spreader portion 22 of the elongated and slender toe spreader 12, with the toe spreader portion generally isosceles-triangular-shaped upper part 52 of the toe spreader portion 22 of the elongated and slender toe spreader 12 extending coplanarally downwardly therefrom, a toe spreader portion upper part pair of straight and upwardly tapering sides 56 that extend downwardly and outwardly from each end of the toe spreader portion upper part flat apex 54 of the toe spreader portion generally isosceles-triangular-shaped upper part 52 of the toe spreader portion 22 of the elongated and slender toe spreader 12, and a toe spreader portion upper part straight base 58 that has a length to extend past three separated middle toes of the user foot toes 24 of the user foot 26 of the user 20, and is thereby preferably 5" long, so that the elongated and slender toe spreader 12 can be utilized with the user foot 26 of the user 20 of different widths.

The toe spreader portion upper part straight base 58 of the toe spreader portion generally isosceles-triangular-shaped upper part 52 of the toe spreader portion 22 of the elongated and slender toe spreader 12 connects the lower ends of the toe spreader portion upper part pair of straight and upwardly tapering sides 56 of the toe spreader portion generally isosceles-triangular-shaped upper part 52 of the toe spreader portion 22 of the elongated and slender toe spreader 12 to each other.

The toe spreader portion 22 of the elongated and slender toe spreader 12 further has a toe spreader portion rectangular-parallelepiped-shaped lower part 60 that extends downwardly from, and is integrally formed with, the toe spreader portion upper part straight base 58 of the toe spreader portion generally isosceles-triangular-shaped upper part 52 of the toe spreader portion 22 of the elongated and slender toe spreader 12, is coplanar with the toe spreader portion generally isosceles-triangular-shaped upper part 52 of the toe spreader portion 22 of the elongated and slender toe spreader 12, and has a length equivalent to that of the toe spreader portion upper part straight base 58 of the toe spreader portion generally isosceles-triangular-shaped upper part 52 of the toe spreader portion 22 of the elongated and slender toe spreader 12.

The toe spreader portion rectangular-parallelepiped-shaped lower part 60 of the toe spreader portion 22 of the elongated and slender toe spreader 12 further has a toe spreader portion lower part straight lower edge 62, and a toe spreader portion lower part pair of spaced-apart, parallel, and rectangular-shaped faces 64 that extend from the toe spreader portion upper part straight base 58 of the toe spreader portion generally isosceles-triangular-shaped upper part 52 of the toe spreader portion 22 of the elongated and slender toe spreader 12 to the toe spreader portion lower part straight lower edge 62 of the toe spreader portion rectangular-parallelepiped-shaped lower part 60 of the toe spreader portion 22 of the elongated and slender toe spreader 12, and are coplanar with the toe spreader portion generally isosceles-triangular-shaped upper part 52 of the toe spreader portion 22 of the elongated and slender toe spreader 12.

The toe spreader portion lower part straight lower edge 62 of the toe spreader portion rectangular-parallelepiped-shaped lower part 60 of the toe spreader portion 22 of the elongated and slender toe spreader 12 has a toe spreader portion lower part lower edge three spaced-apart and rectangular-shaped lateral toe throughslots 66.

Each toe slot of the toe spreader portion lower part lower edge three spaced-apart and rectangular-shaped lateral toe throughslots 66 in the toe spreader portion lower part straight lower edge 62 of the toe spreader portion rectangular-parallelepiped-shaped lower part 60 of the toe spreader portion 22 of the elongated and slender toe spreader 12 has a width slightly less than that of a toe of the user foot toes 24 of the user foot 26 of the user 20 and is thereby preferably 1" wide, so that the elongated and slender toe spreader 12 can be used with the user foot toes 24 of the user foot 26 of the user 20 of different sizes.

The toe spreader portion lower part lower edge three spaced-apart and rectangular-shaped lateral toe throughslots 66 in the toe spreader portion lower part straight lower edge 62 of the toe spreader portion rectangular-parallelepiped-shaped lower part 60 of the toe spreader portion 22 of the elongated and slender toe spreader 12 open into, and extend vertically upwardly from, the toe spreader portion lower part straight lower edge 62 of the toe spreader portion rectangular-parallelepiped-shaped lower part 60 of the toe spreader portion 22 of the elongated and slender toe spreader 12 to the toe spreader portion upper part straight base 58 of the toe spreader portion generally isosceles-triangular-shaped upper part 52 of the toe spreader portion 22 of the elongated and slender toe spreader 12, and extend laterally between, and open into, the toe spreader portion lower part pair of spaced-apart, parallel, and rectangular-shaped faces 64 of the toe spreader portion rectangular-parallelepiped-shaped lower part 60 of the toe spreader portion 22 of the elongated and slender toe spreader 12.

Figure 4:
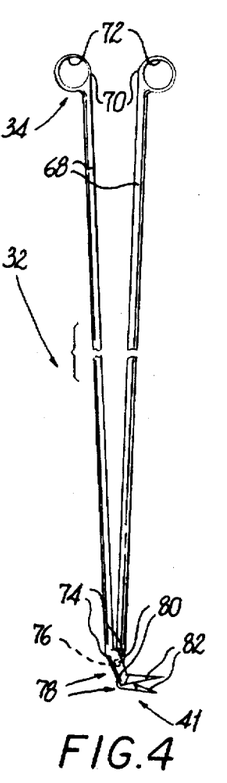
FIG. 4 is a diagrammatic front elevational view of the toe nail scissor of the present invention.

The configuration of the elongated and slender toe nail scissor 32 can best be seen in FIG. 4, which is a diagrammatic front elevational view of the toe nail scissor of the present invention, and as such will be discussed with reference thereto.

The elongated and slender toe nail scissor 32 has a length that extends from the user hand thumb 36 and the user hand index finger 38 of the another user hand 40 of the user 20 to the user foot toes 24 of the user foot 26 of the user 20 and is thereby preferably 42" in length, so that the Loot toe nails 42 of the user foot toes 24 of the user foot 26 of the user 20 can be cut without the user 20 having to bend.

The elongated and slender toe nail scissor 32 further has a toe nail scissor pair of elongated and slender bodies 68 that have a length equivalent to the combined length of the toe spreader slender handle portion 14 and the toe spreader elongated, slender, and generally rectangular-parallelepiped-shaped body 44.

Each body of the toe nail scissor pair of elongated and slender bodies 68 of the elongated and slender toe nail scissor 32 has a toe nail scissor body proximal end 70 from which each toe nail scissor handle portion 34 of the elongated and slender toe nail scissor 32 outwardly extends.

Each toe nail scissor handle portion 34 of the elongated and slender toe nail scissor 32 is a toe nail scissor handle portion closed finger loop 72 that extends outwardly from, and is coplanar with, the toe nail scissor body proximal end 70 of a respective body of the toe nail scissor pair of elongated and slender bodies 68 of the elongated and slender toe nail scissor 32, and has a diameter sufficient to releasibly capture one of the user hand thumb 36 and the user hand index finger 38 of the another user hand 40 of the user 20, so that the combination toe spreader and toe nail scissor 10 is maintained in the another user hand 40 of the user 20 during use.

Each body of the toe nail scissor pair of elongated and slender bodies 68 of the elongated and slender toe nail scissor 32 further has a toe nail scissor body distal end 74. The toe nail scissor body distal end 74 of each body of the toe nail scissor pair of elongated and slender bodies 68 of the elongated and slender toe nail scissor 32 are pivotally connected to each other by a toe nail scissor body distal end pivot pin 76 that maintains the toe nail scissor handle portion closed finger loop 72 of each toe nail scissor handle portion 34 of the elongated and slender toe nail scissor 32 is opposing alignment with, and in movable relationship to, each other.

The toe nail scissor cutting portion 41 of the elongated and slender toe nail scissor 32 has a height equivalent to that of the toe spreader portion 22 of the elongated and slender toe spreader 12, and includes a toe nail scissor cutting portion pair of substantially L-shaped bodies 78.

Each body of the toe nail scissor cutting portion pair of substantially L-shaped bodies 78 of the toe nail scissor cutting portion 41 of the elongated and slender toe nail scissor 32 has a toe nail scissor cutting portion body vertical part 80 that is integrally formed with, and extends vertically downwardly from, the toe nail scissor body distal end of a respective body of the toe nail scissor pair of elongated and slender bodies 68 of the elongated and slender toe nail scissor 32, with the toe nail scissor cutting portion body vertical part 80 of a respective body of the toe nail scissor cutting portion pair of substantially L-shaped bodies 78 of the toe nail scissor cutting portion 41 of the elongated and slender toe nail scissor 32 being coplanar with the respective body of the toe nail scissor pair of elongated and slender bodies 68 of the elongated and slender toe nail scissor 32.

Each body of the toe nail scissor cutting portion pair of substantially L-shaped bodies 78 of the toe nail scissor cutting portion 41 of the elongated and slender toe nail scissor 32 further has a toe nail scissor cutting portion body pointed horizontal cutting part 82 that is integrally formed with, and extends generally perpendicularly horizontally outwardly from, the lower end of the toe nail scissor cutting portion body vertical part 80 of the respective body of the toe nail scissor cutting portion pair of substantially L-shaped bodies 78 of the toe nail scissor cutting portion 41 of the elongated and slender toe nail scissor 32, with the toe nail scissor cutting portion body pointed horizontal cutting part 82 of the respective body of the toe nail scissor cutting portion pair of substantially L-shaped bodies 78 of the toe nail scissor cutting portion 41 of the elongated and slender toe nail scissor 32 being coplanar with the toe nail scissor cutting portion body vertical part 80 of the respective body of the toe nail scissor cutting portion pair of substantially L-shaped bodies 78 of the toe nail scissor cutting portion 41 of the elongated and slender toe nail scissor 32, and being coplanar with the toe nail scissor handle portion closed finger loop 72 of each toe nail scissor handle portion 34 of the elongated and slender toe nail scissor 32.

The toe nail scissor cutting portion body pointed horizontal cutting part 82 of each body of the toe nail scissor cutting portion pair of substantially L-shaped bodies 78 of the toe nail scissor cutting portion 41 of the elongated and slender toe nail scissor 32 point in the same direction.

With the toe nail scissor cutting portion body pointed horizontal cutting part 82 of each body of the toe nail scissor cutting portion pair of substantially L-shaped bodies 78 of the toe nail scissor cutting portion 41 of the elongated and slender toe nail scissor 32 pointing in the same direction, and with their extending outwardly from the lower end of the toe nail scissor cutting portion body vertical part 80 of the respective body of the toe nail scissor cutting portion pair of substantially L-shaped bodies 78 of the toe nail scissor cutting portion 41 of the elongated and slender toe nail scissor 32 provides an offset, so that the foot toe nails 42 of the user foot toes 24 of the user foot 26 of the user 20 can be cut from the side of the user foot 26 of the user 20 without the user 29 having to bend.

It is to be understood that the configurations of the various components of the present invention are not merely a matter of design choice but are significant and of critical importance for, inter alia, the functions that they accomplish as discussed, supra, and any not explicitly expressed but inherent thereto. They therefore must be considered in determining patentability. Support for this assertion can be found in In re Dailey et al., 149 U.S.P.Q. 47 (CCPA 1976), where the Court held that the shape of a device must be considered in determining patentability, if the shape is significant:

"... the configuration of the container is a 'mere matter of choice' not significantly novel . . . , [since]. . . Appellants have provided no argument which convinces us that the particular configuration of their container is significant . . ." [Emphasis added]

The method of using the combination toe spreader and toe nail scissor 10 can best be seen in FIGS. 1 and 2, which are an exploded diagrammatic perspective view of the present invention interfacing with the toes of a user and an enlarged diagrammatic perspective view of the present invention interfacing with the toes of a user, respectively, and as such will be discussed with reference thereto.

STEP 1: Place the user foot pad 30 on a generally horizontal surface.

STEP 2: Place the user foot 26 of the user 20 on the user foot pad 30, with the user foot ball 28 of the user foot 26 of the user 20 resting thereon.

STEP 3: Hold the toe spreader slender handle portion 14 of the elongated and slender toe spreader 12 in the user hand palm 16 of the user hand 18 of the user 20, with the elongated and slender toe spreader 12 pointing downwardly.

STEP 4: Hold the toe nail scissor handle portion 34 of the elongated and slender toe nail scissor 32 in the another user hand 40 of the user 20, with the toe nail scissor handle portion closed finger loop 72 of each toe nail scissor handle portion 34 of the elongated and slender toe nail scissor 32 receiving one of the user hand thumb 36 and the user hand index finger 38 of the another user hand 40 of the user 20, and with the elongated and slender toe nail scissor 32 pointing downwardly.

STEP 5: Position the toe spreader portion lower part straight lower edge 62 of the toe spreader portion rectangular-parallelepiped-shaped lower part 60 of the toe spreader portion 22 of the elongated and slender toe spreader 12 on the tops of the user foot toes 24 of the user foot 26 of the user 20.

STEP 6: Exert a downward force on the elongated and slender toe spreader 12 and thereby cause the toe spreader portion lower part lower edge three spaced-apart and rectangular-shaped lateral toe throughslots 66 in the toe spreader portion lower part straight lower edge 62 of the toe spreader portion rectangular-parallelepiped-shaped lower part 60 of the toe spreader portion 22 of the elongated and slender toe spreader 12 to deform accordingly, and capture, the three middle toes of the user foot toes 24 of the user foot 26 of the user 20 and thereby cause the three middle toes of the user foot toes 24 of the user foot 26 of the user 20 to separate from each other, while the vertical sides of the toe spreader portion rectangular-parallelepiped-shaped lower part 60 of the toe spreader portion 22 of the elongated and slender toe spreader 12 cause the first toe and the fifth toe of the user foot toes 24 of the user foot 26 of the user 20 to separate from the separated three middle toes of the user foot toes 24 of the user foot 26 of the user 20, so that the user foot toes 24 of the user foot 26 of the user 20 are separated from each other without the user 20 having to bend and hold then apart with the user another hand 40 of the user 20.

STEP 7: Cut the user foot toe nails 42 of the separated user foot toes 24 of the user foot 26 of the user 20 with the toe nail scissor cutting portion 41 of the elongated and slender toe nail scissor 32 without the user 20 having to bend, so that the user foot toes 24 of the user foot 26 of the user 20 are separated from each other and the user foot toe nails 42 of the separated user foot toes 24 of the user foot 26 of the user 20 are cut without the user 20 having to bend.

It will be understood that each of the elements described above, or two or more together, may also find a useful application in other types of constructions differing from the types described above.

While the invention has been illustrated and described as embodied in a combination toe spreader and toe scissor, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A pedicure kit, comprising:
   a) an elongated and slender toe spreader having a slender handle portion being releasibly engagable in the palm of the hand of a user, and a toe spreader portion being remote from said slender handle portion of said elongated and slender toe spreader and releasibly engaging and separating the toes of the foot of the user from each other without the user having to bend, so that the toes of the foot of the user who has difficulty bending can be separated from each other without the user having to bend and separate the toes of the foot of the user with the other hand of the user; said elongated and slender toe spreader further having an elongated, slender, and generally rectangular-parallelepiped-shaped body with a proximal end from which said slender handle portion of said elongated and slender toe spreader extends coplanarally upwardly, and a distal end from which said toe spreader portion of said elongated and slender toe spreader extends coplanarally downwardly; said slender handle portion of said elongated and slender toe spreader, being narrower than said elongated, slender, and generally rectangular-parallelepiped-shaped body of said elongated and slender toe spreader so as to provide a pair of lateral shoulders, so that a stop is provided when the palm of the hand of the user grips said slender handle portion of said elongated and slender toe spreader that prevents downward slipping thereof; and
   b) an elongated and slender toe nail scissor being separate from said elongated and slender toe spreader and having a handle portion releasibly engagable by the thumb and the index finger of the other hand of the user, and a cutting portion remote from said handle portion of said elongated and slender toe nail scissor and cutting the toe nails on the toes of the foot of the user without the user having to bend, so that the toe nails on the toes of the foot of the user who has difficulty bending can be cut without the user having to bend.

2. The kit as defined in claim 1, wherein said elongated and slender toe spreader has a length that extends from the palm of the hand of the user to the toes of the foot of the user, so that the toes of the foot of the user can be separated from each other without the user having to bend.

3. The kit as defined in claim 2, wherein said length of said elongated and slender toe spreader is 42".

4. The kit as defined in claim 1, wherein said toe spreader portion of said elongated and slender toe spreader is slightly deformable, so that the toes of the foot of the user of different sizes can be adjusted for.

5. The kit as defined in claim 4, wherein said slightly deformable toe spreader portion of said elongated and slender toe spreader is rubber.

6. The kit as defined in claim 1, wherein said toe spreader portion of said elongated and slender toe spreader has a generally isosceles-triangular-shaped upper part with an isosceles triangular shape; said isosceles triangular shape of said generally isosceles-triangular-shaped upper part of said toe spreader portion of said elongated and slender toe spreader provides an even distribution of a downward force exerted on the toes of the foot of the user by the hand of the user pushing downwardly on said slender handle portion of said elongated and slender toe spreader, so that the toes of the foot of the user can be easily separated from each other.

7. The kit as defined in claim 6, wherein said generally isosceles-triangular-shaped upper part of said toe spreader portion of said elongated and slender toe spreader has a flat apex that is equivalently configured to said distal end of said elongated, slender, and generally rectangular-parallelepiped-shaped body of said elongated and slender toe spreader, with said generally isosceles-triangular-shaped upper part of said toe spreader portion of said elongated and slender toe spreader extending coplanarally downwardly therefrom, a pair of straight and upwardly tapering sides that have lower ends and extend downwardly and outwardly from each end of said flat apex of said generally isosceles-triangular-shaped upper part of said toe spreader portion of said elongated and slender toe spreader, and a straight base that has a length to extend past three separated middle toes of the toes of the foot of the user, so that said elongated and slender toe spreader can be utilized on the foot of the user of different widths; said straight base of said generally isosceles-triangular-shaped upper part of said toe spreader portion of said elongated and slender toe spreader connects said lower ends of said pair of straight and upwardly tapering sides of said generally isosceles-triangular-shaped upper part of said toe spreader portion of said elongated and slender toe spreader to each other.

8. The kit as defined in claim 7, wherein said straight base of said generally isosceles-triangular-shaped upper part of said toe spreader portion of said elongated and slender toe spreader is 5" long.

9. The kit as defined in claim 7, wherein said toe spreader portion of said elongated and slender toe spreader further has a generally rectangular-parallelepiped-shaped lower part that extends downwardly from, and is integrally formed with, said straight base of said generally isosceles-triangular-shaped upper part of said toe spreader portion of said elongated and slender toe spreader, is coplanar with said generally isosceles-triangular-shaped upper part of said toe spreader portion of said elongated and slender toe spreader, and has a length equivalent to that of said straight base of said generally isosceles-triangular-shaped upper part of said toe spreader portion of said elongated and slender toe spreader.

10. The kit as defined in claim 9, wherein said rectangular-parallelepiped-shaped lower part of said toe spreader portion of said elongated and slender toe spreader further has a straight lower edge, and a pair of spaced-apart, parallel, and generally rectangular-shaped faces that extend from said straight base of said generally isosceles-triangular-shaped upper part of said toe spreader portion of said elongated and slender toe spreader to said straight lower edge of said generally rectangular-parallelepiped-shaped lower part of said toe spreader portion of said elongated and slender toe spreader, and are coplanar with said generally isosceles-triangular-shaped upper part of said toe spreader portion of said elongated and slender toe spreader.

11. The kit as defined in claim 10, wherein said straight lower edge of said rectangular-parallelepiped-shaped lower part of said toe spreader portion of said elongated and slender toe spreader has three spaced-apart and generally rectangular-shaped lateral toe throughslots; each toe slot of said three spaced-apart and generally rectangular-shaped lateral toe throughslots in said straight lower edge of said generally rectangular-parallelepiped-shaped lower part of said toe spreader portion of said elongated and slender toe spreader has a width slightly less than that of a toe of the toes of the foot of the user, so that said elongated and slender toe spreader can be used with the toes of the foot of the user of different sizes.

12. The kit as defined in claim 11, wherein said width of each toe slot of said three spaced-apart and generally rectangular-shaped lateral toe throughslots in said straight lower edge of said generally rectangular-parallelepiped-shaped lower part of said toe spreader portion of said elongated and slender toe spreader is 1".

13. The kit as defined in claim 11, wherein said three spaced-apart and generally rectangular-shaped lateral toe throughslots in said straight lower edge of said generally rectangular-parallelepiped-shaped lower part of said toe spreader portion of said elongated and slender toe spreader open into, and extend vertically upwardly from, said straight lower edge of said generally rectangular-parallelepiped-shaped lower part of said toe spreader portion of said elongated and slender toe spreader to said straight base of said generally isosceles-triangular-shaped upper part of said toe spreader portion of said elongated and slender toe spreader, and extend laterally between, and open into, said pair of spaced-apart, parallel, and generally rectangular-shaped faces of said generally rectangular-parallelepiped-shaped lower part of said toe spreader portion of said elongated and slender toe spreader.

14. The kit as defined in claim 1, wherein said elongated and slender toe nail scissor has a length that extends from the thumb and the index finger of the other hand of the user to the toes of the foot of the user, so that the toe nails on the toes of the foot of the user can be cut without the user having to bend.

15. The kit as defined in claim 14, wherein said length of said elongated and slender toe nail scissor is 42".

16. The kit as defined in claim 1, wherein said elongated and slender toe nail scissor has a pair of elongated and slender bodies that each have a length equivalent to combined length of said slender handle portion of said elongated and slender -toe spreader and said elongated, slender, and generally rectangular-parallelepiped-shaped body of said elongated and slender toe spreader.

17. The kit as defined in claim 16, wherein each body of said pair of elongated and slender bodies of said elongated and slender toe nail scissor has a proximal end from which each handle portion of said elongated and slender toe nail scissor outwardly extends.

18. The kit as defined in claim 17, wherein each handle portion of said elongated and slender toe nail scissor is a closed finger loop that extends outwardly from, and is coplanar with, said proximal end of a respective body of said pair of elongated and slender bodies of said elongated and slender toe nail scissor, and has a diameter sufficient to releasibly capture one of the thumb the index finger of the other hand of the user, so that said elongated and slender toe nail scissor is maintained in the other hand of the user during use and is prevented from dropping therefrom.

19. The kit as defined in claim 18, wherein each body of said pair of elongated and slender bodies of said elongated and slender toe nail scissor further has a distal end; said distal end of each body of said pair of elongated and slender bodies of said elongated and slender toe nail scissor are pivotally connected to each other by a pivot pin that maintains said closed finger loop of each handle portion of said elongated and slender toe nail scissor in opposing alignment with, and in movable relationship to, each other.

20. The kit as defined in claim 19, wherein said cutting portion of said elongated and slender toe nail scissor has a height equivalent to that of said toe spreader portion of said elongated and slender toe spreader, and includes a pair of substantially L-shaped bodies.

21. The kit as defined in claim 20, wherein each body of said pair of substantially L-shaped bodies of said cutting portion of said elongated and slender toe nail scissor has a vertical part with a lower end and which is integrally formed with, and extends vertically downwardly from, said distal end of a respective body of said pair of elongated and slender bodies of said elongated and slender toe nail scissor, with said vertical part of a respective body of said pair of substantially L-shaped bodies of said cutting portion of said elongated and slender toe nail scissor being coplanar with said respective body of said pair of elongated and slender bodies of said elongated and slender toe nail scissor.

22. The kit as defined in claim 21, wherein each body of said pair of substantially L-shaped bodies of said cutting portion of said elongated and slender toe nail scissor further has an outwardly converging pointed horizontal cutting part that is integrally formed with, and extends generally perpendicularly horizontally outwardly from, said lower end of said vertical part of said respective body of said pair of substantially L-shaped bodies of said cutting portion of said elongated and slender toe nail scissor, with said outwardly converging pointed horizontal cutting part of said respective body of said pair of substantially L-shaped bodies of said cutting portion of said elongated and slender toe nail scissor being coplanar with said vertical part of said respective body of said pair of substantially L-shaped bodies of said cutting portion of said elongated and slender toe nail scissor, being coplanar with said closed finger loop of each said handle portion of said elongated and slender toe nail scissor, and pointing in the same direction as each other, so that the toe nails on the toes of the foot of the user can be cut from the side of the foot of the user without the user having to bend.

23. The kit as defined in claim 1; further comprising a foot pad being trapezoidal-shaped and having a length extending transversely across the ball of the foot of the user, and a width extending longitudinally along the ball of the foot of the user, so that a comfortable place is provided to rest the foot of the user when the toe nails on the toes of the foot of the user are being cut, while elevating the toes of the foot of the user.

24. The kit as defined in claim 23, wherein said foot pad is rubber.

25. A method of providing a pedicure, comprising said steps of:

a) placing a user foot pad of said pedicure kit on a generally horizontal surface;

b) placing the foot of a user on said foot pad, with the ball of the foot of the user resting thereon;

c) holding a handle portion of an elongated and slender toe spreader of said pedicure kit in the palm of the hand of the user, with said elongated and slender toe spreader pointing downwardly;

d) holding a handle portion of an elongated and slender toe nail scissor of said pedicure kit in the other hand of the user, with a closed finger loop of each said handle portion of said elongated and slender toe nail scissor receiving one of the thumb and the index finger of the other hand of the user, and with said elongated and slender toe nail scissor pointing downwardly;

e) positioning a straight lower edge of a generally rectangular-parallelepiped-shaped lower part of a toe spreader portion of said elongated and slender toe spreader on the tops of the toes of the foot of the user;

f) exerting a downward force on said elongated and slender toe spreader and thereby cause three spaced-apart and generally rectangular-shaped lateral toe throughslots in said straight lower edge of said generally rectangular-parallelepiped-shaped lower part of said toe spreader portion of said elongated and slender toe spreader to slightly deform accordingly, and capture, three middle toes of the toes of the foot of the user and thereby cause the three middle toes of the toes of the foot of the user to separate from each other, while vertical sides of said generally rectangular-parallelepiped-shaped lower part of said toe spreader portion of said elongated and slender toe spreader cause a first toe and a fifth toe of the toes of the foot of the user to separate from the separated three middle toes of the toes of the foot of the user, so that the toes of the foot of the user who has difficulty bending can be separated from each other without the user having to bend and hold the toes of the foot of the user apart with the other hand of the user; and g) cutting the toe nails on the separated toes of the foot of the user with a cutting portion of said elongated and slender toe nail scissor without the user having to bend, so that the toe nails on the toes of the foot of the user who has difficulty bending can be cut without the user having to bend.

\* \* \* \* \*